US010195329B2

(12) United States Patent
Koch et al.

(10) Patent No.: US 10,195,329 B2
(45) Date of Patent: Feb. 5, 2019

(54) METHOD OF MANUFACTURING A CONCENTRATE

(71) Applicant: Fresenius Medical Care Deutschland GmbH, Bad Homburg (DE)

(72) Inventors: Michael Koch, Gerolzhofen (DE); Achim Eberlein, Schweinfurt (DE); Joachim Noack, Bad Neustadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 806 days.

(21) Appl. No.: 14/168,406

(22) Filed: Jan. 30, 2014

(65) Prior Publication Data

US 2014/0209520 A1    Jul. 31, 2014

Related U.S. Application Data

(60) Provisional application No. 61/758,470, filed on Jan. 30, 2013.

(30) Foreign Application Priority Data

Jan. 30, 2013  (DE) .................. 10 2013 001 628

(51) Int. Cl.
| | | |
|---|---|---|
| *A61M 1/16* | (2006.01) | |
| *B01F 1/00* | (2006.01) | |
| *B01F 15/00* | (2006.01) | |

(52) U.S. Cl.
CPC ......... *A61M 1/1666* (2014.02); *B01F 1/0005* (2013.01); *B01F 15/0022* (2013.01);
(Continued)

(58) Field of Classification Search
None
See application file for complete search history.

(56) References Cited

U.S. PATENT DOCUMENTS 5,295,505 A * 3/1994 Polaschegg ......... A61M 1/1656
                                                              137/93
5,318,750 A    6/1994 Lascombes
(Continued)

FOREIGN PATENT DOCUMENTS

| | | |
|---|---|---|
| DE | 3443911 | 6/1986 |
| DE | 9418915 | 2/1995 |

(Continued)

OTHER PUBLICATIONS

Chinese Office Action dated Jun. 24, 2016.

*Primary Examiner* — Patrick J Orme
(74) *Attorney, Agent, or Firm* — Jacobson Holman, PLLC.

(57) ABSTRACT

A method of providing a concentrate of a dissolved substance for producing a dialysis solution includes providing a container containing a solid to be dissolved, supplying water into the container for dissolving the solid, draining the concentrate of the dissolved substance from the container and topping up with water, measuring the concentration of the dissolved substance or of a parameter correlated with the concentration, and temporary or permanent suppression of the topping up of water into the container. The suppression is effected when the measured concentration value of the dissolved substance falls below a first limit value or the value of the parameter falls below or exceeds a first limit value or when the change in the concentration value of the dissolved substance or of the value of the parameter exceeds a first limit value.

18 Claims, 3 Drawing Sheets

(52) U.S. Cl.
CPC ..... *A61M 2205/18* (2013.01); *A61M 2205/33* (2013.01); *A61M 2205/70* (2013.01)

(56) References Cited

U.S. PATENT DOCUMENTS

| | | | |
|---|---|---|---|
| 5,348,389 A | | 9/1994 | Jonsson et al. |
| 6,113,793 A | * | 9/2000 | Jonsson ................ A61L 2/0023 210/636 |

FOREIGN PATENT DOCUMENTS

| | | |
|---|---|---|
| DE | 69114319 | 4/1996 |
| DE | 29710097 | 11/1997 |
| EP | 0556098 | 8/1993 |
| EP | 0714668 | 6/1996 |
| TW | 200612989 | 5/2006 |

* cited by examiner

METHOD OF MANUFACTURING A CONCENTRATE

CROSS-REFERENCE TO RELATED APPLICATIONS

This application claims benefit to U.S. Provisional Application No. 61/758,470, filed Jan. 30, 2013.

BACKGROUND OF THE INVENTION

1. Field of Invention

The present invention relates to a method of providing a concentrate of at least one dissolved substance for producing a dialysate solution.

2. Description of the Prior Art

On a dialysis treatment with an online production of the dialysis solution, a bag having solid sodium carbonate is usually used for providing the alkaline concentrate.

Water from the dialysis machine is introduced into this bag prior to the start of treatment and thus a saturated solution of the sodium bicarbonate is produced. The monitoring of the filling level of the liquid or of the solid/liquid mixture in the bag takes place by a pressure measurement in devices known from the prior art. If a predefined pressure value is not reached, water is topped up in the bag. The removed quantity of liquid is thus replaced by fresh water as soon as the pressure in the bag falls below a threshold, that is, a pressure-controlled topping up of the water takes place. As soon as the sodium carbonate contained in the bag has dissolved, a saturated solution can no longer be produced and the concentration of the solution in the bag falls accordingly.

If the concentration falls below a specific value, the required quantity of sodium carbonate can no longer be conveyed or utilized by an eccentric membrane pump or by any other conveying member for producing a dialysis solution and a bicarbonate alarm occurs.

This has the consequence that the user has to remove the still filled bag from the dialysis machine and has to attach a new bag which is filled with the solid to be dissolved or the treatment must be ended prematurely.

At this point in time, the previously used bag is, however, still filled, and indeed with an insufficiently concentrated bicarbonate solution which has to be discarded even though the solution to be discarded still contains bicarbonate.

SUMMARY OF THE INVENTION

It is therefore the object of the present invention to further develop a method of the initially named kind such that the bag content can be ideally utilized, whereby unnecessary waste is avoided.

This object is achieved by a method having the features of claim 1. Provision is accordingly made that the method comprises the following steps:
  providing at least one container containing at least one solid to be dissolved;
  supplying water into the container for dissolving the solid;
  draining the concentrate of the dissolved substance from the container and topping up with water;
  measuring the concentration of the dissolved substance or of a parameter correlated with this concentration;
  and temporary or permanent suppression of the topping up of water into the container when the measured concentration value of the dissolved substance falls below a first limit value or the value of the correlated parameter falls below or exceeds a first limit value or when the change in the concentration value of the dissolved substance or of the value of the correlated parameter exceeds a first limit value.

It is thus the underlying idea of the present invention to set the topping up with water permanently or temporarily when, for example, the conductivity or another parameter by means of which a conclusion can be drawn on the concentration falls below a limit value or exceeds it. If the topping up with water is suppressed before the concentration in the bag falls below a critical level, the residual bicarbonate quantity located in the bag or the quantity of the other dissolved substance can still be completely used up or utilized for the use of the dialysis solution.

This not only brings about the advantage that the still present dissolved substance in the container preferably formed as a bag can be largely or completely used and waste is avoided, but also that the dialysis can still be continued until the bag has been completely emptied.

Optionally, the use of an additional or new bag or other container shortly before the end of the treatment can be avoided under certain circumstances. Under certain circumstances, an online reinfusion can also still be carried out and thus an additional bag with saline solution can be saved.

It is the main idea of the present invention to suppress the topping up of water into the bag when the conductivity or another parameter correlated with the concentration of the dissolved substance in the bag falls below or exceeds a limit value. This parameter can, for example, be the conductivity, the transmission, the absorption, etc. If the conductivity, concentration, etc. is in an acceptable range, the filling and emptying of the container runs in the normal range; e.g., in this case the topping up with water can run with pressure control, i.e. if the pressure falls below a limit value, water is topped up until an upper limit value for the pressure is reached.

On an exceeding or falling below of the limit value in accordance with the invention for the concentration, conductivity, etc., a switchover is made from normal operation into an operating mode in which the topping up is permanently or temporarily suppressed.

Provision can alternatively or additionally be made that e.g. a time-based or volume-related change or another change in the conductivity or of another parameter correlated with the concentration is detected and—if this change exceeds a specific boundary—the bag or other container is no longer topped up for a specific time or permanently.

It is thus conceivable, for example, that the gradient of the conductivity over time is measured. If it exceeds a specific limit value, provision can be made that the topping up with water is at least temporarily suppressed. The same applies accordingly e.g. to a volume-related change. If, for example, the conductivity per volume unit removed from the bag changes, a gradient can be formed from the conductivity change and the volume change and a decision can be made on this basis whether a topping up with water is suppressed or not.

It is conceivable that the concentration value no longer rises, but rather falls due to the dilution occurring on the further supply of water because the solid has completely dissolved. It is, however, also conceivable that the concentration value rises again or that the gradient of the conductivity changes again over time or the gradient of the conductivity change over the volume changes again, and indeed when only a temporary problem with the dissolving process of the solid to be dissolved occurred. If the dissolving process restarts, this results in an increase in the concentration so that a return can again be made to the normal operating mode in which a topping up with water takes place e.g. by pressure control.

If the concentration should also no longer increase after a switching off of the topping up routine, i.e. after switching off the normal operation, it can be assumed that the bicarbonate or the at least one substance otherwise to be dissolved has been completely dissolved. In this case, liquid can be conveyed from the bag or other container and can be used for producing the dialysis solution for so long unit it is empty. This state can be recognized, for example, by a lack of liquid at the level sensor in the bicarbonate chamber or by the lack of excess pressure in the container.

As long as the concentration, the conductivity of the liquid located in or removed from the container or another value correlated therewith lies in an acceptable range, the control or the regulation of the supply of water to the container can take place e.g. in dependence on the pressure in the container, in dependence on the conductivity or on its time development or on the concentration of the removed solution or its time development, in dependence on the removed volume from the container, on the required bicarbonate concentration for a sufficient metering or critical limit from which onward a sufficient metering can no longer take place.

If the topping up with water is suppressed from a specific limit onward, this brings about the advantage that too great a dilution is avoided and that the concentrate still located in the container can be used for producing the dialysate solution.

In a preferred embodiment of the invention, the concentration of the dissolved substance or the correlated parameter in the concentrate running out of the container is measured. Alternatively to this, a measurement of the concentration or of the other parameter in the bag itself would be conceivable.

Provision is made in a further embodiment of the invention that the change in the concentration value of the dissolved substance or of the parameter value is—as stated above—the change per time unit or is the change per volume unit removed from the container. In these cases, a gradient dS/dt or dS/dV is formed, where S stands for the conductivity, t for the time and V for the volume removed from the container. If these gradients exceed a specific limit value, a decision can be made that the topping up of water stops at least temporarily, i.e. the normal operating mode is switched off. If, for example a change in the gradient or an increase in the concentration in a desired range occurs due to a dissolving process starting again, provision can be made that the topping up process with water and thus the normal operation is reactivated.

Provision is made in a preferred embodiment that the container is preferably completely emptied if it is determined after the suppression of the topping up with water that the concentration value of the dissolved substance or the value of the parameter correlated with the concentration is no longer rising or no change in the trend (falling/rising) occurs. If e.g. an increase in the concentration no longer occurs, a conclusion can be drawn that a solid to be dissolved is no longer present and that the supply of further water would only result in a still further dilution and thus in a concentration reduction. In this case, the fact remains in this respect that no water is topped up and the bag is preferably completely emptied.

As already stated above, it is conceivable that the topping up with water is activated again if it is found that the concentration value of the dissolved substance or the value of the parameter correlated with the concentration again lies in an acceptable range, for instance because local dissolving processes restart again.

It is conceivable that the first limit value is formed by a critical limit value and a supplement.

The minimally permitted value for the conductivity of the solution flowing from the container or of the concentrate depends on the desired target concentration. The required quantity of bicarbonate results from the relationship $$c_{desired} \times V_{balance\ chamber} < V_{max} \times c_{min}$$

where $V_{max}$ is the maximum conveying volume of the bicarbonate pump, e.g. 2.2 ml. If a setting ($e_{desired}$) for bicarbonate of 35 mmol bicarbonate and 30 ml balance chamber volume is assumed, a minimal concentration ($c_{min}$) results in the container or bag of 477 mmol/l. A minimal conductivity of approximately 29.5 mS/cm results from this. This minimal conductivity can be the critical limit value. If it is fallen below, the solution located in the container for producing a dialysis solution can no longer be used since it is diluted too much.

To maintain a specific "safety interval" from this critical limit, it may be meaningful that the first limit value is formed by this critical limit value and a supplement. This means that the suppression of the topping up is not only initiated when the named critical limit value is reached, but rather when the first limit value is reached which is spaced apart from the critical limit value by a supplement. It is, for example, conceivable to set a 20% reserve, which in the named example would mean that the suppression of the topping up already takes place a value of the conductivity of 34 mS/cm. If the conductivity then increases again so that the minimum concentration, i.e. the critical limit, is exceeded by e.g. 30%, topping up can again take place or the usual topping up routine can be initiated again.

It is thus conceivable that the topping up with water is activated again when the concentration value of the dissolved substance or the value of the parameter correlated with the concentration or the change dS/dt or dS/dv etc. exceeds a second limit value.

The second limit value can lie above the first limit value so that the method is operated with a certain hysteresis.

Provision can furthermore be made that the first and/or second limit value is/are spaced apart from the critical value by a percentage amount, for example in the range from 20-30%.

Provision can furthermore be made that the at least one dissolved substance is only or also bicarbonate, preferably sodium bicarbonate. Provision is made in a preferred embodiment of the invention that the dissolved substance is the so-called alkaline concentrate which is used within the framework of the production of a dialysis solution.

The water can be RO (reverse osmosis) water.

It is pointed out at this point that the term "water" within the framework of the present invention not only comprises RO water, but rather any desired solvent.

The present invention furthermore relates to a dialysis machine having the features of claim 11. This dialysis machine is equipped with at least one connector port to which at least one container comprising a solid to be dissolved is or can be connected, wherein the dialysis machine furthermore has at least one supply line for the supply of water into the container and at least one removal line for the removal of concentrate from the container and wherein the dialysis machine furthermore has at least one sensor for measuring the concentration or for measuring a parameter correlated therewith of the concentrate removed from the container or located therein.

Provision is made in accordance with the invention that the dialysis machine has at least one control or regulation unit which is configured so that it carries out the provision of a concentrate of a dissolved substance from the container in accordance with one of the above-named claims 1 to 10. This means, in other words, that the control or regulation unit is configured such that it can operate the dialysis machine in accordance with this method in accordance with the invention.

The dialysis machine thus has means for the online production of a dialysis solution which are operated in accordance with the method in accordance with the invention.

The named sensor of the dialysis machine can be a conductivity sensor. Concentration sensors and also any desired other kind of sensors are generally covered by the invention whose measured values allow a conclusion on the concentration of the at least one dissolved substance.

The dialysis machine can have at least one unit for producing RO water or can have at least one connector through which RO water can be supplied to the dialysis machine. The water supplied to the container can accordingly be RO water.

It is conceivable that the machine has a main line and a branched off secondary line in which the at least one container is located. After flowing through the container, the correspondingly formed concentrate is mixed with the RO water of the main line so that a dialysis solution is present in the desired concentration. A dilution of the concentrate by RO water thus takes place at the mixing point.

Provision can furthermore be made that the dialysis machine has setting means by means of which the first limit value and/or the second limit value and/or the critical limit value and/or the named supplement to the critical limit value can be set by a user.

Provision can furthermore be made that the dialysis machine has means for emitting an alarm when the first limit value and/or the second limit value and/or the critical limit value is exceeded or fallen below.

The invention further relates to the use of at least one container which contains at least one solid to be dissolved in a method and/or in a dialysis machine in accordance with the present invention. The solid to be dissolved can be bicarbonate or the solid can comprise bicarbonate.

BRIEF DESCRIPTION OF THE DRAWINGS

Further details and advantages of the invention will be explained in more detail with reference to an embodiment shown in the drawing. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The Figures and the embodiment described in the following relate to the dissolving of bicarbonate or to a bicarbonate concentrate.

Figure 1:
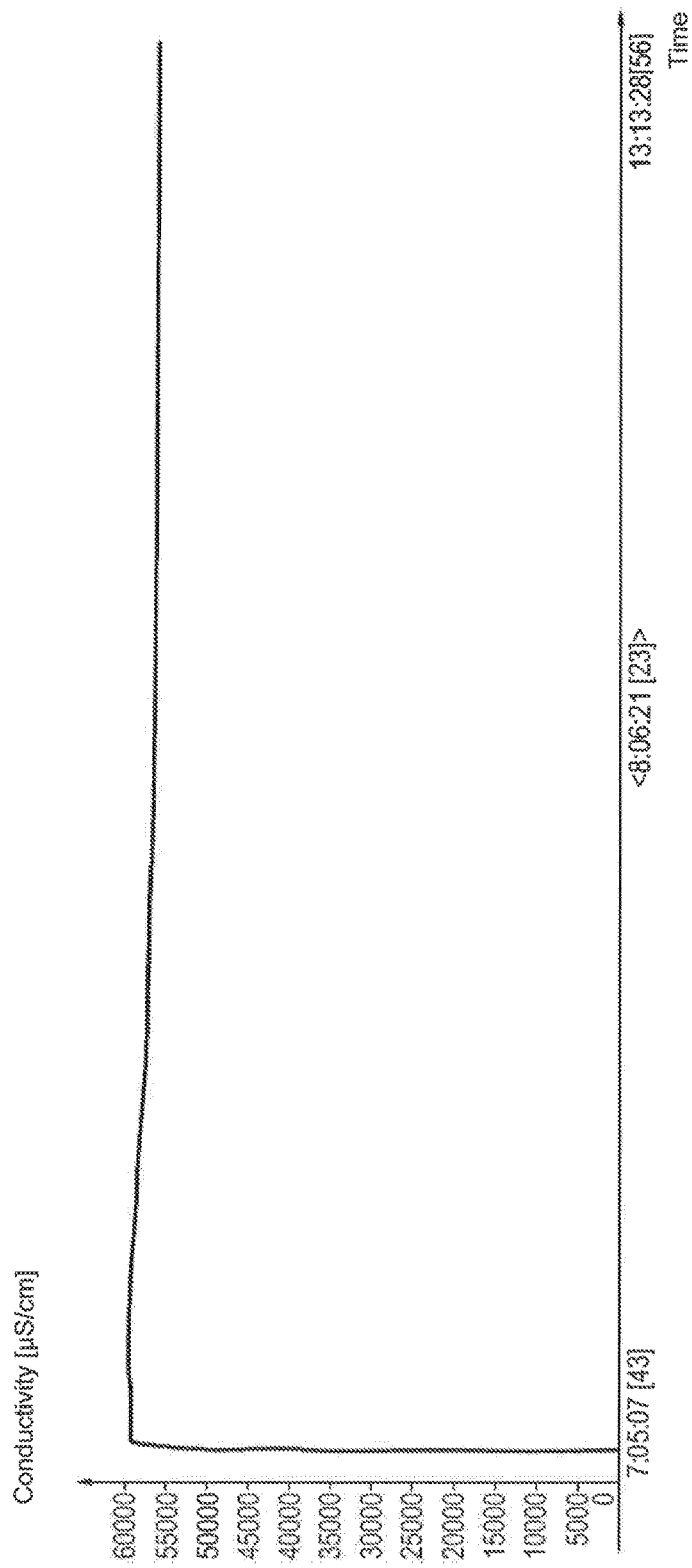
FIG. 1: a time development of the conductivity of the concentrate running out of a bag over time.

It can be seen from FIG. 1 that the concentrate produced online and running out of the bag has a substantially constant conductivity and thus concentration within the course of the dialysis process. This concentration can correspond to the saturation concentration of the dissolved substance(s) or can substantially correspond to this saturation concentration. FIG. 1 thus shows a typical development of the conductivity of the liquid removed from a bag during a treatment without the bag change (temperature-compensated).

Figure 2:
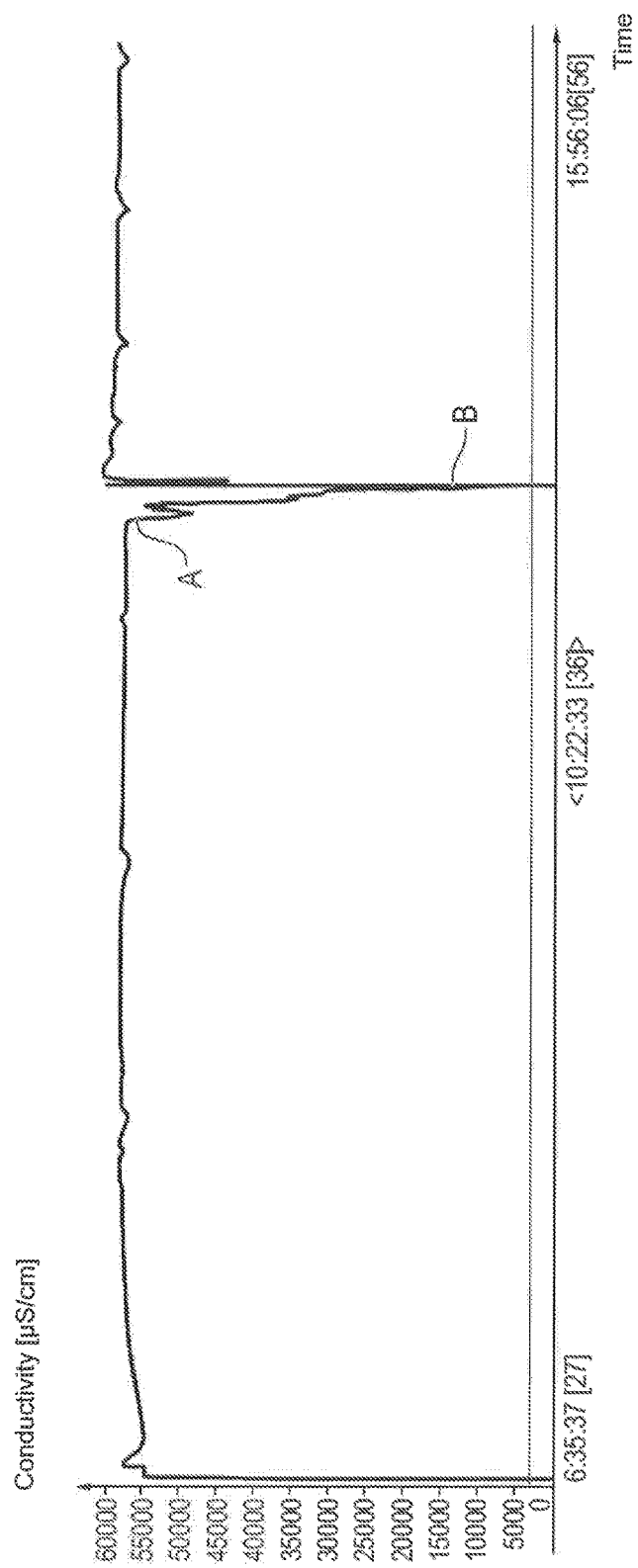
FIG. 2: the development of the conductivity of a concentrate running out of the bag over time with an undershoot of the bicarbonate concentration and with a change of the bag.

FIG. 2 shows that from a specific point in time A onward an undershoot, that is a great drop in the conductivity and thus in the concentration, of the liquid removed from the bag takes place. This undershoot of the conductivity in the example shown here takes place 13 minutes before the bicarbonate alarm or before the conductivity alarm at the time B. The dialysate flow amounted to 940 ml/min. Around 400 ml was removed from the bag in the time up to the bicarbonate alarm.

The concentration c in the bag results in accordance with the following equation $$c[\text{mmol/l}] = 10 + 11.52 \times LF(25°\text{ C.})[\text{mS/cm}] 0.156 (LF(25°\text{ C.})[\text{mS/cm}])^2.$$

In a full bag, the conductivity of the solution lies at around 57 mS/cm, as can be seen from FIG. 2. This corresponds to a concentration of around 1173 mmol/l.

As already stated above, the minimally permitted value for the conductivity depends on the wanted desired concentration. In the above-named example, a minimal conductivity of 29.5 mS/cm results. This is a good match to the occurrence of the bicarbonate alarm in accordance with FIG. 2. This value was fallen below 40 s before the alarm emission B in the embodiment shown here.

In the embodiment shown in FIG. 2, the bag was changed at the time B, that is, at the time of the occurrence of the bicarbonate alarm, that is, the full bag was removed and a new bag with fresh solid was attached to the dialysis machine. The bag was then filled with water and a conductivity in the range from around 57 mS/cm was again adopted, as can be seen from FIG. 2.

Figure 3:
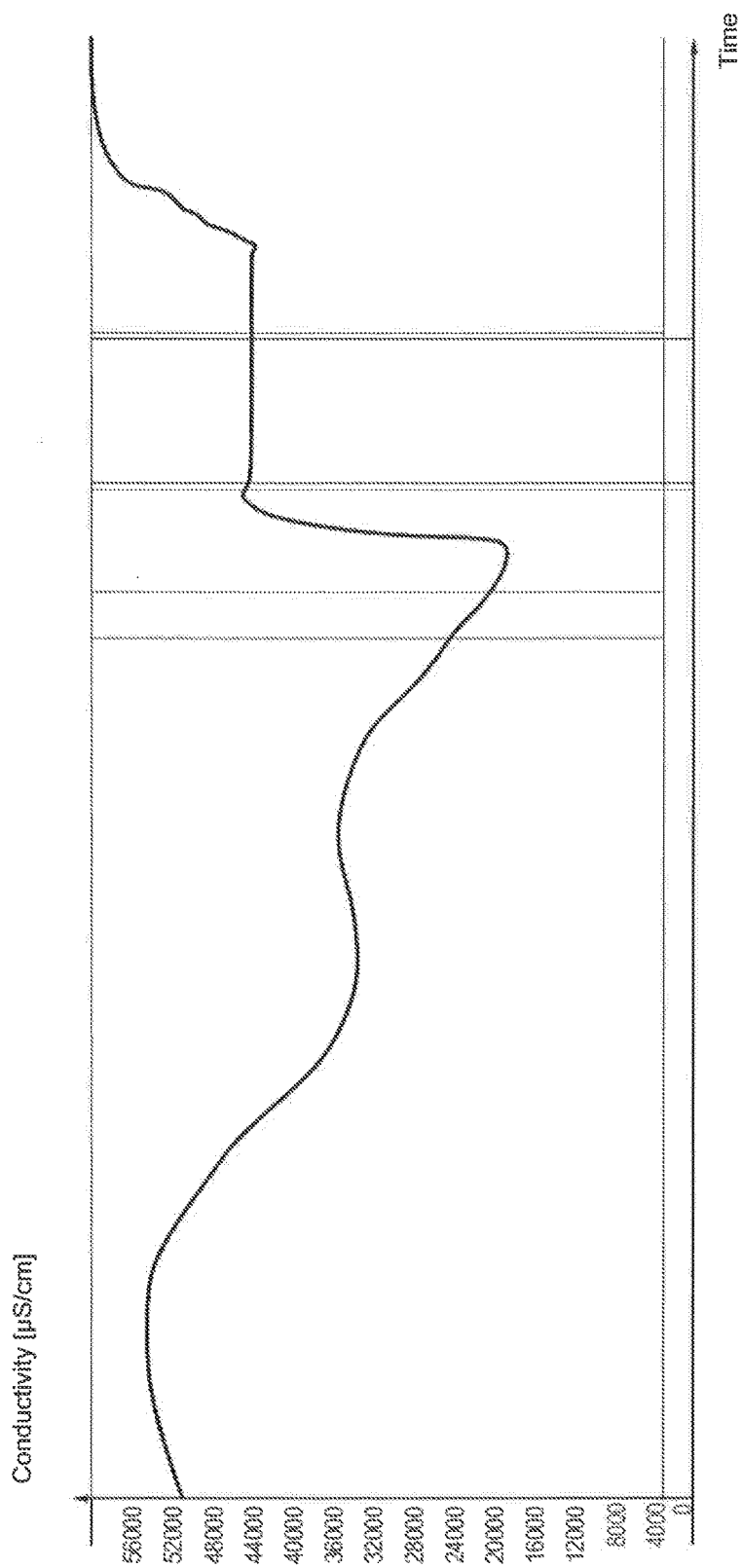
FIG. 3: an enlarged view of the conductivity development in accordance with FIG. 2 in the range of large conductivity changes.

FIG. 3 shows the time section of the drop in conductivity in accordance with FIG. 2 in an enlarged representation.

As can be seen from FIG. 3, in the embodiment shown here, the bag was replaced at a conductivity value of round 20 mS/cm. The bag with this concentration was discarded and a new bag was used.

It is now possible in accordance with the invention to prevent too great a drop in the concentration as shown in FIG. 3 in that a topping up with water is stopped from a specific limit value of the conductivity onward. This has the result that the concentration in the bag remains at a specific minimum level; in the specific example, for example, a value of 34 mS/cm as a first limit value could be meaningful.

If the conductivity then rises again because dissolving processes start again, topping up can again take place or a switch to the topping up mode can be made.

This may be the case, for example, if the minimum concentration, that is the critical value is exceeded e.g. by 30%.

It can be stated overall that waste can be avoided by the present invention and that furthermore, depending on the overall treatment time required, the advantage can be achieved that the attachment of a bag or container containing new solid to be dissolved to the device can optionally be avoided.

The dialysis treatment can thus be continued until the bag has been completely emptied. The attachment of a further bag shortly before the end of the treatment is hereby stopped or avoided under certain circumstances and optionally an online reinfusion can be carried out.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of providing a a dialysis solution, the method comprising the following steps:
    providing a dissolving vessel containing a water-soluble solid substance;
    supplying water into the dissolving vessel to dissolve the solid substance and provide a concentrate comprising the solid substance in a dissolved state thereof;
    draining the concentrate from the dissolving vessel while simultaneously supplying fresh water into the dissolving vessel to fully replace a drained volume of the concentrate; and
    measuring a concentration of the dissolved solid substance in the concentrate, either directly or via a correlated parameter, and, if the concentration falls below a set boundary value or if a change in the concentration exceeds a set boundary value, stopping or reducing the fresh water supply into the dissolving vessel while continuing to drain the concentrate from the dissolving vessel without full replacement of the drained volume by the supply of the fresh water,
    with all of the concentrate drained from the dissolving vessel being further diluted on-line to provide the dialysis solution.

2. The method in accordance with claim 1, wherein the concentration of the dissolved solid substance or the correlated parameter in the concentrate being drained from the dissolving vessel is measured.

3. The method in accordance with claim 1, wherein a change of the concentration of the dissolved solid substance or of the correlated parameter is the change per time unit or the change per volume unit taken from the dissolving vessel.

4. The method in accordance with claim 1, wherein the dissolving vessel is completely emptied when it is found that the concentration of the dissolved solid substance is no longer increasing, or the value of the correlated parameter is no longer increasing or is no longer decreasing.

5. The method in accordance with claim 1, wherein the water is reverse osmosis water.

6. The method in accordance with claim 1, wherein the set boundary value represents a critical value and a supplement.

7. The method in accordance with claim 1, wherein the step of supplying water is activated again when the concentration of the dissolved solid substance exceeds a second set boundary value, or when the value of the correlated parameter exceeds or falls below e the second set boundary value.

8. The method in accordance with claim 7, wherein the second set boundary value lies above or below the set boundary value or corresponds thereto.

9. The method in accordance with claim 7, wherein at least one of the set boundary value and the second set boundary value lies above or below a critical value by a percentage amount.

10. The method in accordance with claim 1, wherein the dissolved solid substance is a bicarbonate or includes a bicarbonate.

11. The method according to claim 10, wherein the bicarbonate is sodium bicarbonate.

12. A dialysis machine comprising:
    a connector port to which a dissolving vessel having a water-soluble solid substance to be dissolved therein is connected or is connectable;
    a supply line for supplying water into the dissolving vessel so as to dissolve the solid substance and provide a concentrate comprising the solid substance in a dissolved state thereof, and a removal line for removing the concentrate from the dissolving vessel;
    a sensor for measuring a concentration of the concentrate removed from the dissolving vessel, or for measuring a parameter correlated therewith; and
    a control or regulation unit configured to effect the providing of the concentrate of the dissolved solid substance from the dissolving vessel in accordance with the method of claim 1.

13. The dialysis machine in accordance with claim 12, wherein the sensor is a conductivity sensor.

14. The dialysis machine in accordance with claim 12, further comprising a unit for producing reverse osmosis water or a connector through which reverse osmosis water is supplied to the dialysis machine, and wherein the water supplied to the dissolving vessel is the reverse osmosis water.

15. The dialysis machine in accordance with claim 12, further comprising an element for setting by a user the set boundary value and/or a second set boundary value and/or a critical boundary value and/or a supplement to the critical boundary value.

16. The dialysis machine in accordance with claim 12, further comprising an element that emits an alarm when the set boundary value and/or a second set boundary value and/or a critical boundary value is/are exceeded or fallen below.

17. The dialysis machine in accordance with claim 12, wherein the solid substance is a bicarbonate or includes a bicarbonate.

18. The dialysis machine in accordance with claim 17, wherein the bicarbonate is sodium bicarbonate.

* * * * *